(12) United States Patent
Badami et al.

(10) Patent No.: US 7,426,039 B2
(45) Date of Patent: Sep. 16, 2008

(54) OPTICALLY BALANCED INSTRUMENT FOR HIGH ACCURACY MEASUREMENT OF DIMENSIONAL CHANGE

(75) Inventors: Vivek G Badami, Pittsford, NY (US); Steven R Patterson, Livermore, CA (US)

(73) Assignee: Corning Incorporated, Corning, NY (US)

( * ) Notice: Subject to any disclaimer, the term of this patent is extended or adjusted under 35 U.S.C. 154(b) by 264 days.

(21) Appl. No.: 11/338,127

(22) Filed: Jan. 23, 2006

(65) Prior Publication Data

US 2006/0132794 A1    Jun. 22, 2006

Related U.S. Application Data

(63) Continuation-in-part of application No. 10/900,484, filed on Jul. 27, 2004, now Pat. No. 7,239,397.

(60) Provisional application No. 60/533,810, filed on Dec. 31, 2003.

(51) Int. Cl.
*G01B 9/02* (2006.01)

(52) U.S. Cl. .................................... 356/503

(58) Field of Classification Search ............ 356/503, 356/485–487, 492, 498, 493, 495, 511–514
See application file for complete search history.

(56) References Cited

U.S. PATENT DOCUMENTS

| 6,504,615 B1 * | 1/2003 | Abe et al. ............ 356/511 |
| 7,173,715 B2 * | 2/2007 | Mueller et al. ........ 356/503 |
| 7,239,397 B2 * | 7/2007 | Badami et al. ........ 356/503 |

OTHER PUBLICATIONS

M. Okaji, N. Yamada, K. Nara, and H. Kato entitled "Laser interferometric dilatometer at low temperatures: application to fused silica SRM 739," Cryogenics 35, pp. 887-891, 1995.

\* cited by examiner

*Primary Examiner*—Hwa (Andrew) S Lee
(74) *Attorney, Agent, or Firm*—Timothy M. Schaeberle

(57) ABSTRACT

An instrument for measuring dimensional changes in materials, such as ultra-low thermal expansion materials, contains an optically balanced measuring loop. Both an object beam and a loop beam propagate around the measuring loop. The object beam encounters both opposite side surfaces of the test object and the loop beam encounters remaining components of the measuring loop in common with the object beam. The object and loop beams can be separately compared to reference beams for producing heterodyne signal beams.

29 Claims, 10 Drawing Sheets

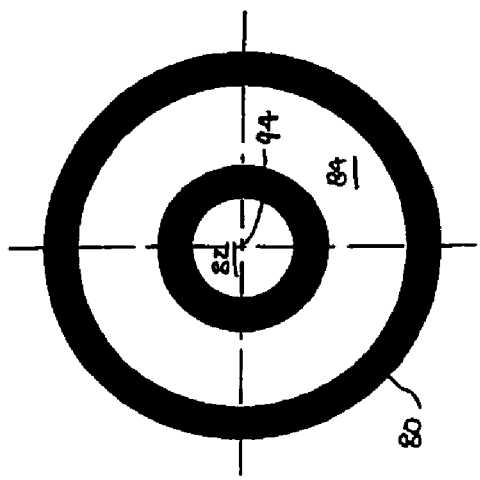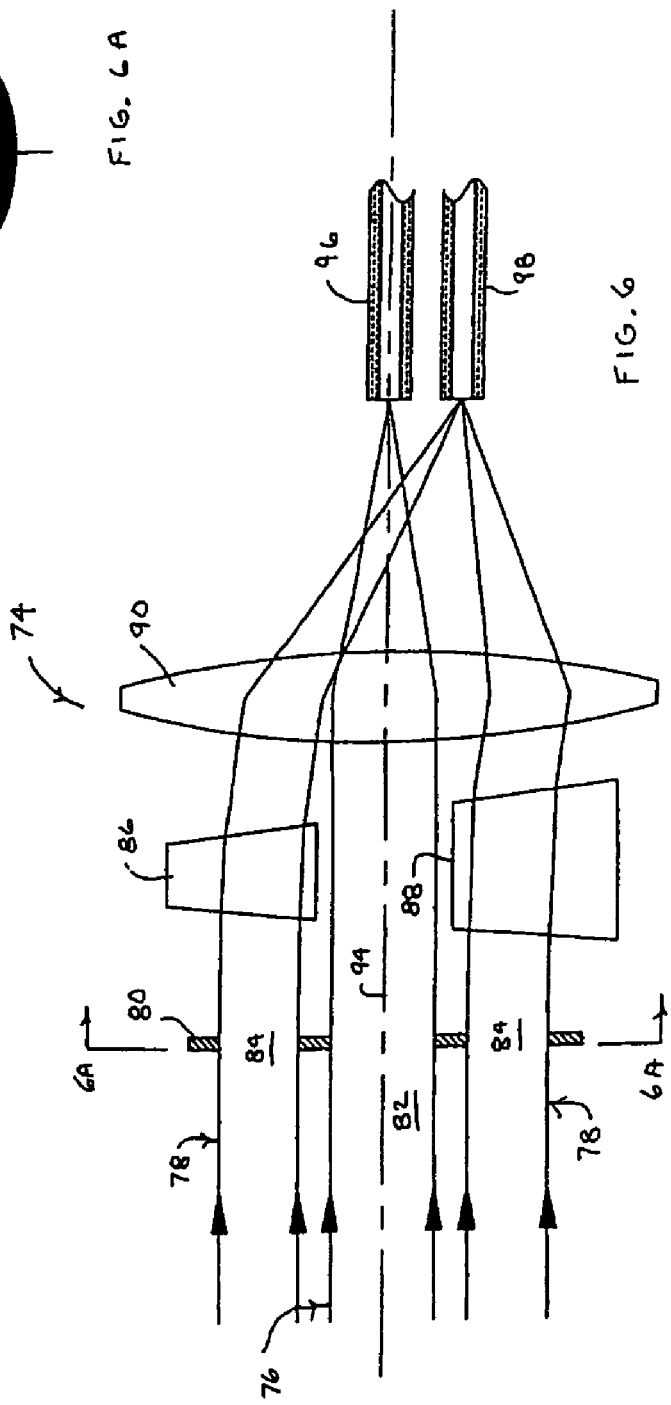

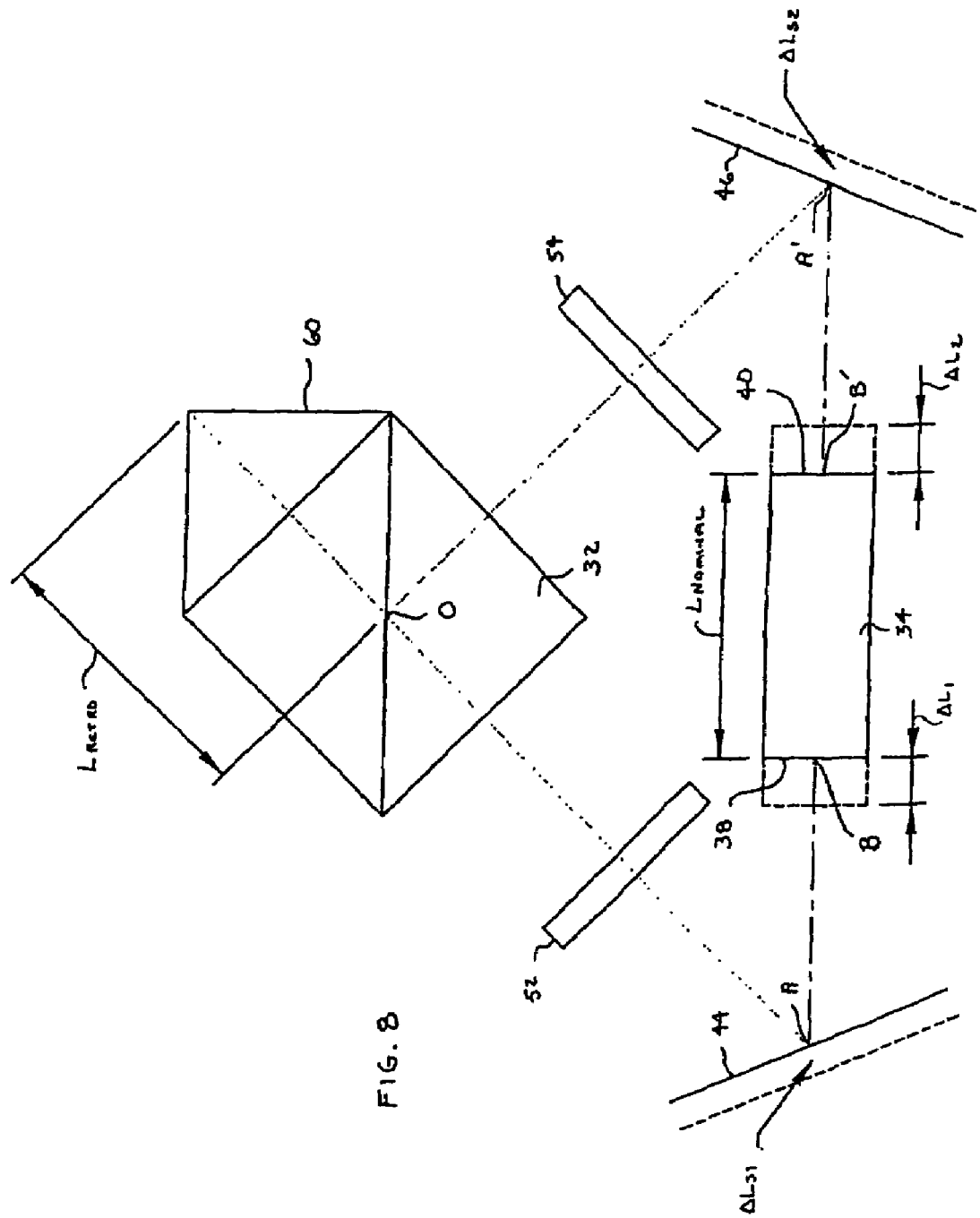

US 7,426,039 B2

OPTICALLY BALANCED INSTRUMENT FOR HIGH ACCURACY MEASUREMENT OF DIMENSIONAL CHANGE

CROSS-REFERENCE TO RELATED APPLICATIONS

This application is a continuation-in-part of U.S. application Ser. No. 10/900,484 filed on Jul. 27, 2004 now U.S. Pat. No. 7,239,397 for a Device for High Accuracy Measurement of Dimensional Changes, which claims priority to U.S. Provisional Application No. 60/533,810 filed on Dec. 31, 2003. Both prior applications are hereby incorporated by reference.

TECHNICAL FIELD

The invention relates to precision instruments for measuring dimensional changes of materials, particularly instruments for measuring thermal expansion/contraction characteristics of ultra-low thermal expansion materials.

BACKGROUND OF INVENTION

Ultra-low thermal expansion materials such as ULE® glass (a trademark of Corning Incorporated) and Zerodur® glass (a trademark of Schott Glas) provide dimensional stability for a variety of precision applications including structures requiring significant dimensional stability over a range of temperatures. Examples include structural materials for precision machines and instruments and substrate materials for space optics, telescopes, and extreme ultra-violet lithography (EUVL) optics and photomasks.

For such purposes as calibration, certification, and process feedback, precise measurements are required of the thermal expansion characteristics of these ultra-low expansion materials (referred to as coefficient of thermal expansion measurements or CTE measurements). Since few if any materials exhibit lower thermal expansion characteristics, the instruments used for measuring ultra-low thermal expansion materials are often subject to nearly the same or even greater thermally induced dimensional variations. The CTE measurements are taken at different temperatures by heating or cooling the test material within the measuring instrument. Accompanying thermal deformations of the measuring instrument are generally the largest source of uncertainty in the CTE measurements.

Prior CTE measuring instruments that measure dimensional changes in ultra-low thermal expansion materials using the mechanism of interference have attempted to compensate for such instrument errors in two main ways. Some employ common path interferometry so that local instrument changes equally affect the common path portions of test and reference beams. However, these interferometers have difficulty consistently relating the test and reference beams where the beams depart in the vicinity of the test materials under investigation. Joints and other connections between reference surfaces and the test materials are also significant sources of error. Other CTE measuring instruments include two separate interferometers, one for measuring the test material and the other for simultaneously measuring both the test material and the instrument. The simultaneous measurements are taken along parallel paths. However, the instrument measuring path does not account for all of the spurious variation undergone by the test material measuring path.

SUMMARY OF INVENTION

The invention is directed to achieving high-accuracy measurements of dimensional change, such as CTE (coefficient of thermal expansion) measurements of ultra-low thermal expansion materials. A test object having at least partially reflective opposite side faces can be mounted within a measuring loop within which both an object beam and a loop beam are propagated. In traversing the measuring loop, the object beam encounters both side faces of the test object. With the exception of the two opposite side faces of the test object, the loop beam preferably encounters the same optical components as the object beam within the measuring loop for providing a balanced optical design. The object and loop beams can be compared to a common reference beam to distinguish path length variations between the two opposite side faces of the test object from path length variations of the measuring loop.

One version of the invention as an optical instrument for measuring dimensional changes of a test object between two opposite side faces of the test object includes a measuring loop having a plurality of optical components and a mounting for the test object. A beam routing system routes a measuring beam from a beam source to the measuring loop and from the measuring loop to a data acquisition system. The optical components of the measuring loop (a) circulate a first transverse portion of the measuring beam as an object beam that encounters both of the opposite side faces of the test object and the optical components between entering and exiting the measuring loop and (b) circulate another transverse portion of the measuring beam as a loop beam that encounters the optical components without encountering the two opposite side faces of the test object between entering and exiting the measuring loop. The data acquisition system indirectly compares the object and loop beams to distinguish length variations between the two opposite side faces of the test object and path length variations of the measuring loop.

For purposes of optically balancing the design, the object beam encounters both opposite side faces of the test object and the object and loop beams encounter each of the optical components of the measuring loop the same number of times. In doing so, the object beam preferably encounters each of the two opposite side faces of the test object more than one time to enhance resolution of the measurement. Preferably, the two opposite side faces are substantially flat and at least partially reflective, extend substantially parallel to one another, and overlap each other along the measured length of the test object.

An environmental modifier preferably subjects the test object to varying conditions within the measuring loop. For measuring thermal expansion characteristics of the test object, the environmental modifier can include a heat-regulating device for varying the temperature of the test object. The data acquisition system collects data regarding the length variations of the test object at the different conditions (e.g., temperature) of the test object regulated by the environmental modifier.

The object and loop beams can have the same beam frequencies and the beam routing system can combine the object and loop beams with a different frequency reference beam to form heterodyne signals that vary with path length variations between the object and loop beams. A polarizing beamsplitter can direct the measuring beam into the measuring loop as linearly polarized object and loop beams and waveplates located between the beamsplitter and each of the two opposite side faces of the test object can orthogonally rotate the polarization of the object and loop beams between encounters with the polarizing beamsplitter. A retroreflector can be optically connected to the beamsplitter for returning the object and loop beams to the measuring loop so that the object beam encounters each of the two opposite side faces of the test object more than one time and so that the loop beam encounters each of the optical components of the measuring loop the same number of times as the object beam.

A reflector can be located within the measuring loop for reflecting the loop beam without further reflecting the object beam. The reflector can change the order at which the loop beam encounters components within the measuring loop to match the order at which the object beam encounters the same optical elements in the measuring loop and can also match phase changes that occur at the opposite side faces of the test object. The reflector is preferably made of a base material for supporting opposite side reflective surfaces and the base material of the reflector that matches a base material of the test object. In one arrangement, the reflector has a de minimus thickness in the direction of beam propagation. In another arrangement, the reflector has a nominal length between two opposite side reflective surfaces in a fixed non-unity ratio with a nominal length between the opposite sides surfaces of the test object.

Another version of the invention as an optical instrument for measuring dimensional changes of a test object between two opposite side faces of the test object includes a light source for introducing first and second beams of different primary frequencies. A beam routing system routes the first and second frequency beams, including routing the first frequency beam into a measuring arm. A measuring loop within the measuring arm has a plurality of optical components and a mounting for the test object. The optical components (a) circulate a first transverse portion of the first frequency beam through encounters with both the plurality of optical components and the two opposite side faces of the test object and (b) circulate a second transverse portion of the first frequency beam through encounters with the same optical components without encountering the two opposite side faces of the test object. The beam routing system combines the first and second transverse portions of the first frequency beam with the second frequency beam for producing heterodyne signals that can be evaluated for distinguishing length variations between the two opposite side faces of the test object from path length variations of the remaining measuring loop.

An environmental modifier preferably subjects the test object to varying conditions within the measuring loop. For example, a heat-regulating device can be used for varying the temperature of the test object. A data acquisition system evaluates the length variations between the two opposite side faces of the test object at the different conditions of the test object imposed by the environmental modifier.

The first and second transverse portions of the first frequency beam preferably encounter each of the optical components of the measuring loop the same number of times. The beam routing system can route the second frequency beam into a reference arm. A first beam discriminator can be used to prevent the second frequency beam from entering the measuring loop, and a second beam discriminator can be used to prevent the first frequency beam from propagating through the reference arm. For such purposes, the first and second frequency beams can be orthogonally polarized and the first and second beam discriminators can be formed as polarizers.

The measuring loop preferably includes a beamsplitter for directing the first frequency beam into and out of the measuring loop. The measuring loop also preferably contains waveplates for orthogonally rotating the polarization of the first measuring beam between encounters with the beamsplitter. Beam directors within the measuring loop preferably direct the first transverse portion of the first frequency beam into alignment with the two opposite side faces of the test object and preferably direct the second transverse portion of the first frequency beam along a route that includes the beamsplitter and the beam directors.

A retroreflector can be optically connected to the beamsplitter for returning the first frequency beam to the measuring loop so that the first transverse portion of the first frequency beam encounters each of the two opposite side faces of the test object more than one time. For optically balancing the design, the first and second transverse portions of the first measuring beam preferably encounter each of the optical components of the measuring loop the same number of times.

A reflector can be used to interrupt the loop beam for varying an order through which the loop beam engages the optical components of the measuring loop. The reflector can have a reflective portion and one or more gaps in the reflective portion so that one portion of the loop beam passes through the gap and another portion of the loop beam reflects from the reflective portion. The reflective portion can be a mirror symmetrical about a transverse axis so that the loop beam reflects from opposite sides of the reflector. The reflective portion can be angularly distributed around an optical axis so that the loop beam reflects from one side of the reflector and transmits through the other side of the reflector.

BRIEF DESCRIPTION OF THE DRAWING FIGURES

FIG. 1 is a diagram showing one possible layout of the invention as an instrument for measuring the thermal expansion characteristics of ultra-low thermal expansion materials.

FIG. 2 is a diagram of a measuring loop portion of a test arm within the instrument. Circled reference numerals coupled to arrowheads designate the direction and number of propagations of the measuring beam portions over the same pathways. Following the arrowheads, double arrows perpendicular to the direction of propagation represent a p-polarized state, dots in corresponding positions represent a s-polarized state, and circular arrow patterns represent right and left handed circular polarizations.

FIG. 6 is a depiction of a detector module for separately detecting different transverse portions of a combined measuring and reference beam.

FIG. 6A is an end view of a mask shown in FIG. 6 for physically isolating the different transverse portions of the combined beam.

FIG. 8 is a diagram of the measuring loop of FIG. 1 showing various dimensions.

Figure 9B:
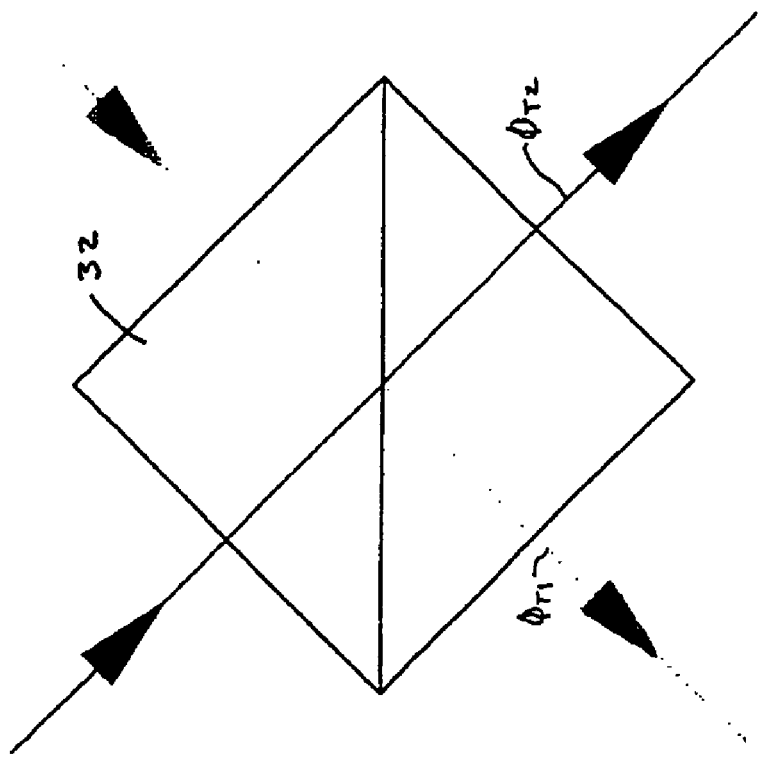
Figure 9A:
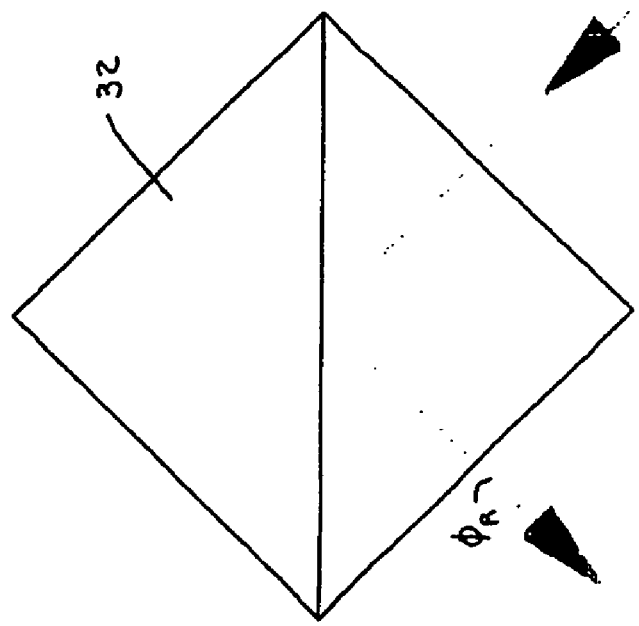

FIGS. 9A and 9B reference the location and direction of phase change terms within a measuring beam router.

Figure 10:
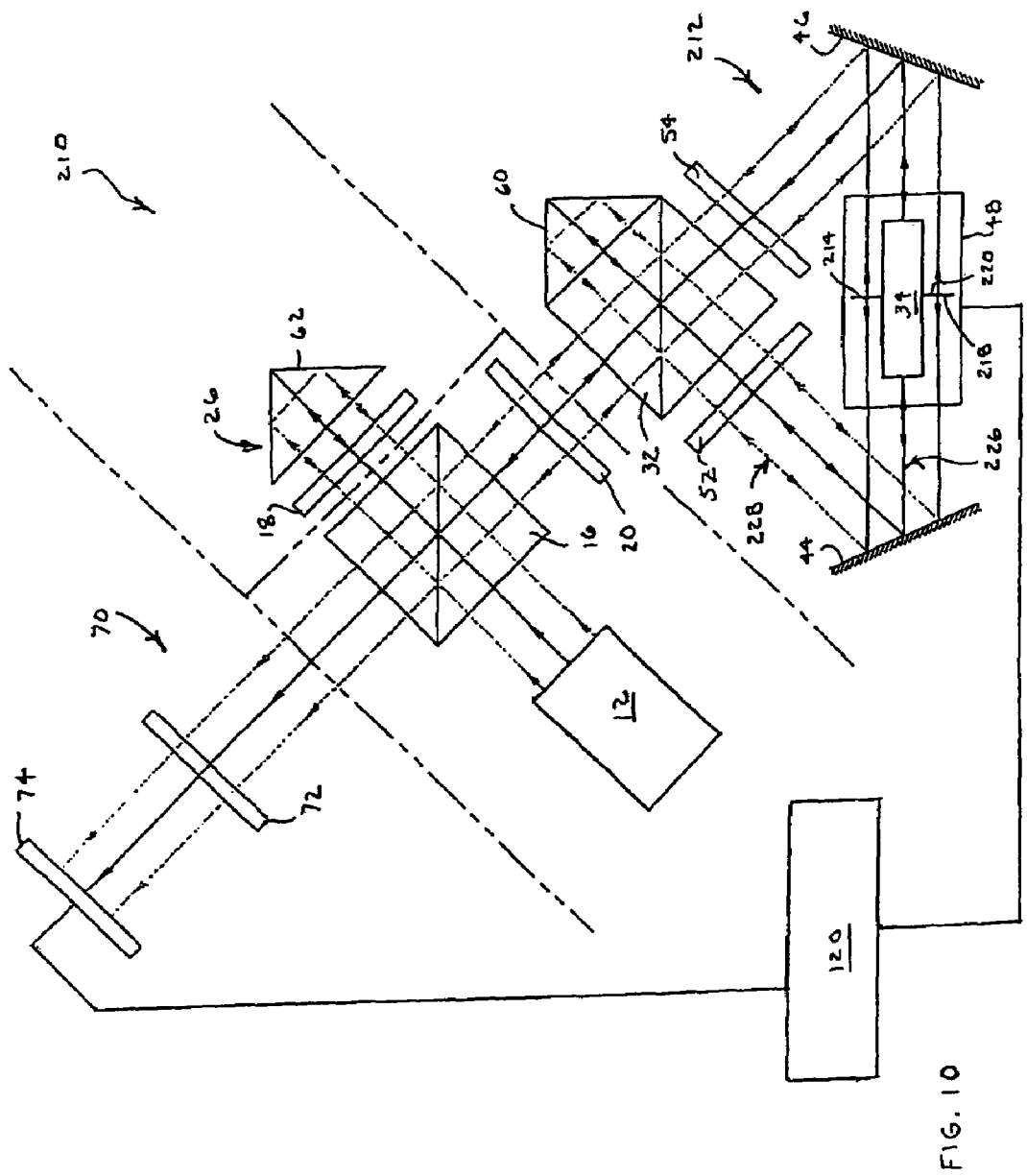

FIG. 10 is a diagram of another alternative instrument in which a reflector is mounted in the measuring loop to match changes in phase change undergone by the loop beam with changes in phase change undergone by the object beam by reflections from opposite side faces of the test object.

DETAILED DESCRIPTION

Figure 1:
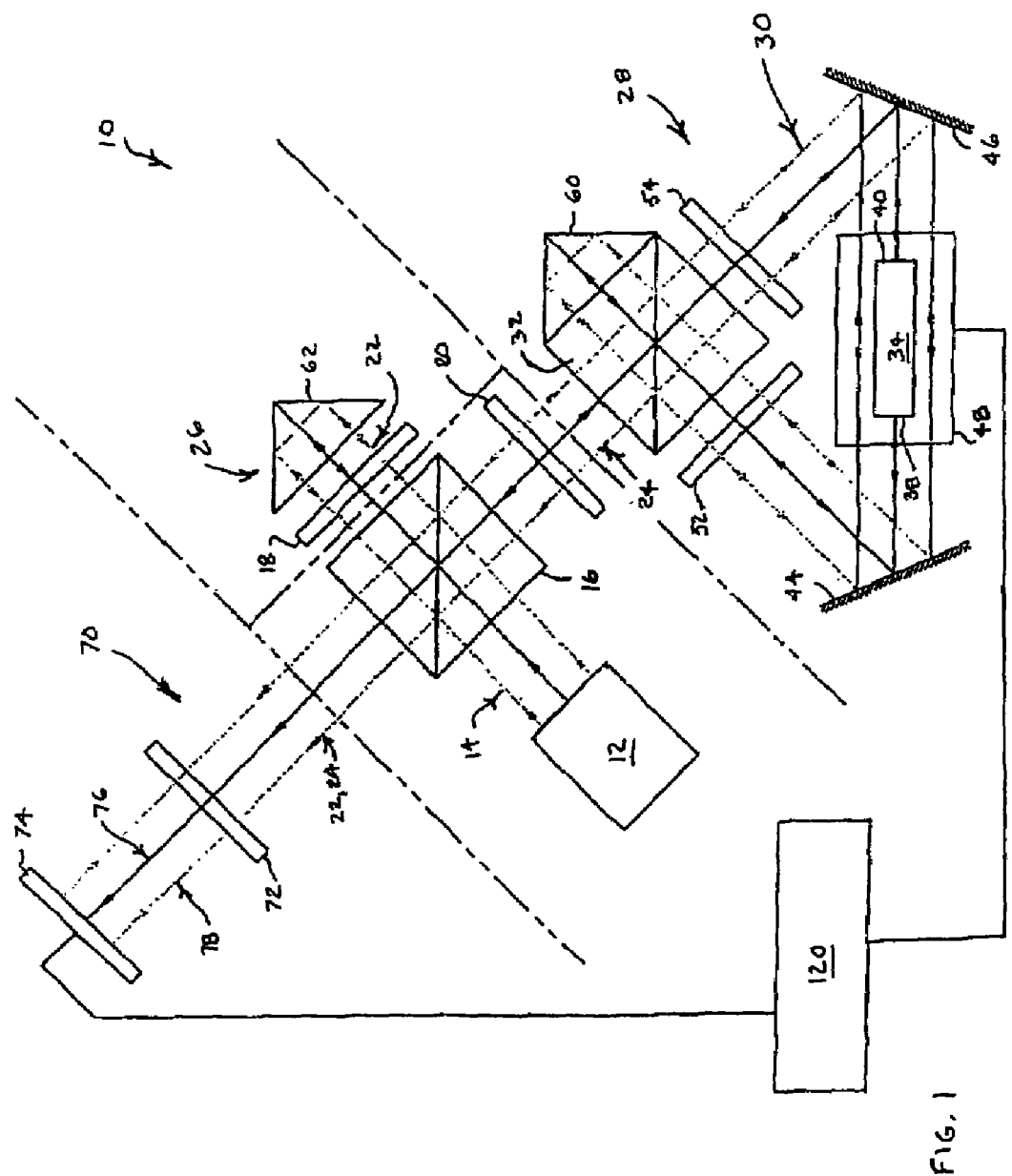

An instrument 10 arranged for the measurement of thermal expansion characteristics of ultra-low thermal expansion materials is laid out in FIG. 1. The instrument 10 has the general configuration of a Michelson interferometer but is specially arranged for making heterodyne displacement measurements of the ultra-low thermal expansion materials. Such materials generally exhibit thermal expansions of less than 30 parts per billion per degree Celsius.

A multi-frequency laser source 12 emits an expanded beam of light 14 having two primary frequencies ($f_1$ and $f_2$) that are linearly polarized in nominally orthogonal states (s and p). The laser source 12 preferably includes a HeNe two-frequency frequency-stabilized laser, such as a 7712 Laserhead from Zygo Corporation, emitting the two primary frequencies ($f_1$ and $f_2$), which together exhibit a beat frequency of approximately 20 megahertz. Higher or lower beat frequencies can be used but all much lower than the average of the frequencies (f1 and f2), since the expected rates of change intended for measurement are slow. The cost of electronic monitoring tends to decrease with lowered beat frequencies. The measurement resolution is set largely by the average of the two frequencies ($f_1$ and $f_2$). A beam expander (not shown) expands the collimated beam to desired dimensions.

A main beam router 16, which is preferably a 50 percent partially reflective beamsplitter, operates together with two orthogonally related polarizers 18 and 20 to divide the two-frequency beam 14 into a transmitted single-frequency ($f_1$) linear-polarized (s) reference beam 22 and a reflected single-frequency ($f_2$) linear-polarized (p) measuring beam 24. The polarizer 18 has a (90 degrees) transmission axis normal to the plane of FIG. 1 for transmitting the referenced "s" linear polarization. The polarizer 20 has a (0 degrees) transmission axis located in the plane of FIG. 1 for transmitting the referenced "p" polarization. The single-frequency ($f_1$) reference beam 22 propagates on a round trip through a reference arm 26, and the single-frequency ($f_2$) measuring beam propagates on a round trip through a measuring arm 28, both single-frequency beams 22 and 24 returning to the main beam router 16 in their respective polarization states (s and p). The orthogonal linear polarizations (s and p) provide a convenient way to separately manipulate the two different frequency ($f_1$ and $f_2$) beams, and as such, can be inverted or otherwise relatively oriented for carrying out this function.

Figure 2:
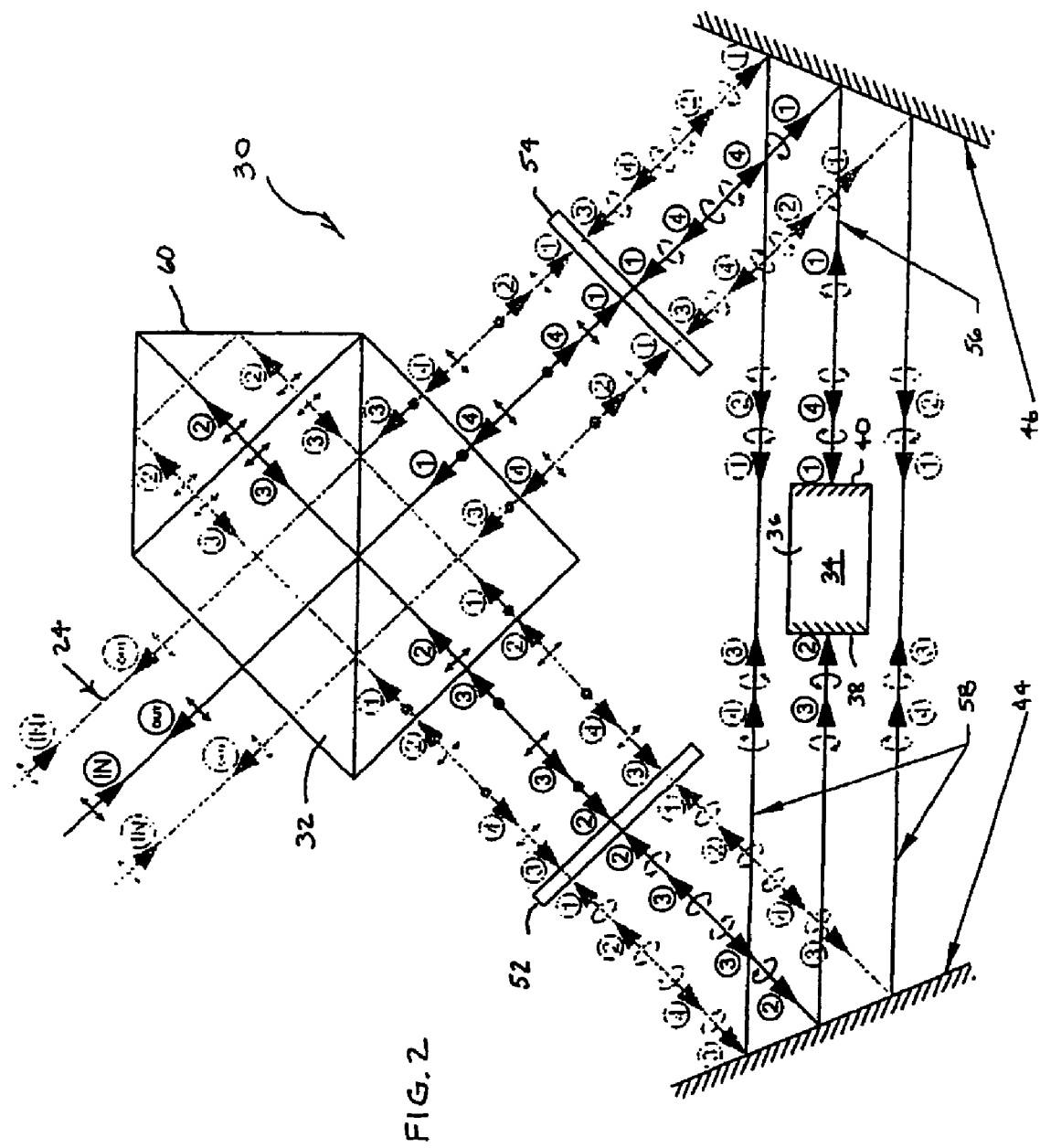

Along the measuring arm 28, also shown in FIG. 2, the measuring beam 24 enters a measuring loop 30 through a measuring beam router 32 in the form of a polarizing beamsplitter oriented for transmitting the measuring beam 24 in its p-polarization state into the measuring loop 30. Within the measuring loop 30, a test object 34 is mounted for measurement. The test object 34 is preferably made from an ultra-low thermal expansion material and preferably has a body 36 with a rectangular cross section and two opposite side surfaces 38 and 40 that are substantially flat, at least partially reflective, and substantially plane parallel. In addition, the two opposite side surfaces 38 and 40 preferably overlap each other along a direction of intended measurement through the measuring loop 30. For example, the test object 34 can take the form of a cylinder, rectangular parallelepiped, or other prismatic structure with plane-parallel opposite ends. The opposite side surfaces 38 and 40 at the ends of the illustrated body 36 are preferably polished or coated to enhance reflectivity. High reflectance metallic or dielectric coatings can be used for this.

Two beam directors 44 and 46 in the form of plane mirrors cooperate with the measuring beam router 32 to complete optical pathways around the measuring loop 30 in an overall triangular configuration with the measuring beam router 32 forming an apex and the two beam directors 44 and 46 forming base vertices. The test object 34 is preferably located between the two beam directors 44 and 46 within an environmental modifier 48, such as a heat regulator, for varying the temperature of the test object 34 between measurements. Although not shown, the test object 34 is preferably mounted on a support, such as a two-point mount that does not restrict expansion of contraction of the length of the test object 34.

Two polarization rotators 52 and 54 in the form of one-quarter waveplates oriented with their fast axes both at +45 degrees to the polarization direction are also located along the measuring loop 30. One of the polarization rotators 52 is located between the opposite side surface 38 and the measuring beam router 32, and the other of the polarization rotators 54 is located between the opposite side surface 40 and the measuring beam router 32. Both polarization rotators 52 and 54 rotate polarization in the same direction, converting a linear polarization to a circular polarization on a first encounter and converting the circular polarization to an orthogonal linear polarization on a second encounter.

The measuring beam 24 enters the measuring loop 30 with a transverse area that is larger that the overlapping area occupied by the opposite side surfaces 38 and 40. For example, the illustrated measuring beam 24 has a diameter that is larger than a diameter of the test object 34. Alternatively, the test object 34 could be formed with a hollow center or in some other configuration to define similar differential areas. A transverse portion of the measuring beam 24 that encounters, i.e., reflects from, the opposite side surfaces 38 and 40 is referred to as an object beam 56, and a remaining transverse portion of the measuring beam 24 that does not encounter the opposite side surfaces 38 and 40 is referred to as a loop beam 58. Both the object beam 56 and the loop beam 58 encounter all of the remaining optical components of the measuring loop 30, including the measuring beam router 32, the two beam directors 42 and 44, and the two polarization rotators 52 and 54.

Upon entry into the measuring loop 30, both the object beam 56 and the loop beam 58 are converted by the polarization rotator 54 to a circular polarization state and reflected from the beam director 46 toward the test object 34 and the other beam director 44. The beam director 46 orients the object beam 56 at normal incidence to the side surface 40 of the test object 34. The object beam 56 preferably reflects from the side surface 40 on a return path to the measuring beam router 32 past both the beam director 46 and the polarization rotator 54. In view of its second encounter with the polarization rotator 54, the object beam 56 arrives back at the measuring beam router 32 with an orthogonal linear polarization (s) and is reflected onward in a counterclockwise direction, propagating through the polarization rotator 52 toward the beam director 44.

The loop beam 58 bypasses the test object 34 entirely and reaches the beam director 44 traveling in the opposite clockwise direction. After reflecting from the beam director 44 and passing through the polarization rotator 52, the loop beam 58 also arrives at the measuring beam router 32 with an orthogonal linear polarization (s) and is reflected onward, continuing in the clockwise direction through the measuring loop 30.

The object beam 56 approaches the opposite side surface 38 of the test object 34 from a counterclockwise direction and is reflected back toward the measuring beam router 32—this time arriving at the measuring beam router 32 with its original linear polarization (p). As such, the object beam 56 transmits through the measuring beam router 32 toward a retroreflector 60, which is optically coupled to the measuring beam router 32. The retroreflector 60 takes the form of a corner cube prism, as shown, to reduce alignment sensitivities. However, the corner cube retroreflector could be replaced with a plane mirror.

The object beam 56 returning from the retroreflector 60 transmits back through the measuring beam router 32 and propagates around the measuring loop 30 in a counterclockwise direction for a second encounter with the opposite end face 38 of the test object 34. Reflection from the opposite side face 38 of the test object 34 redirects the object beam 56 in a clockwise direction around the measuring loop 30, re-approaching the measuring beam router 32 with an orthogonal polarization (s). The measuring beam router 32 reflects the object beam 56 onward in the clockwise direction toward the opposite side face 40. After encountering the opposite side face 40 a second time, the object beam 56 propagates in the counterclockwise direction back to the measuring beam router 32 with its original linear polarization (p) restored. The returning p-polarized object beam 56 transmits through the measuring beam router 32 and exits the measuring loop 30 on a return route through the measuring arm 28 toward the main beam router 16.

Meanwhile, the loop beam 58 continues rounding the measuring loop 30 a second time in the clockwise direction, bypassing the test object 34, and re-approaches the measuring beam router 32 with its original linear polarization (p) restored. The p-polarized loop beam 58 transmits through the measuring beam router 32 to the retroreflector 60, which returns an inverted loop beam 58 for propagating in a counterclockwise direction. Encounters with the polarization rotators 52 and 54 during a first round trip of the loop beam 58 in the counterclockwise direction orthogonally rotate the polarization of the loop beam 58 to the orthogonal polarization state (s), so that upon reencountering the measuring beam router 32, the loop beam 58 is reflected onward for a second round trip in the counterclockwise direction. The original linear polarization state (p) is restored during the second round trip in the counterclockwise direction so that upon return to the measuring beam router 32, the loop beam 58 exits the measuring loop 30 on a return path through the measuring arm 28 toward the main beam router 16.

Between the first and second pairs of encounters of the object beam 56 with the opposite side surfaces 38 and 40 of the test object 34 and between the two clockwise and two counterclockwise laps of the loop beam 58, the retroreflector 60 inverts the object and loop beams 56 and 58 for effectively canceling effects of odd-order errors across the beams. For example, gross rotation of the beam directors 44 or 46 results in beam shear between the reference and measuring beams 22 and 24 rather than an angular misalignment, thus easing alignment requirements. Similarly, gross rotation of the test object 34 also results in beam shear between the reference and measuring beams 22 and 24 rather than an angular misalignment, thus simplifying alignment of the test object 34 and reducing sensitivity to angular motions of the test object 34 during measurement. Non-parallelism of the opposite side faces 38 and 40 of the test object 34 also manifests itself as different amounts of beam shear. The retroreflector 60 also effectively doubles the path lengths of the object and loop beams 56 and 58 within the measuring loop 30, thereby doubling the number of encounters of the object beam 56 with the opposite side surfaces 38 and 40 of the test object 34 for increasing measurement resolution.

Although depicted as being located between the measuring beam router 32 end each of the beam directors 44 and 46, the polarization rotators 52 and 54 can also be located between the beam directors 44 and 46 and the opposite side surfaces 38 and 40 of the test object 34. In this alternative configuration, the beam directors 44 and 46 would be presented with linearly polarized light, which is advantageous for non-normal incidence reflections. Since the object beam encounters both opposite side surfaces 38 and 40 of the test object 34, the test object 34 could also be located elsewhere around the measuring loop 30 such as between one of the beam directors 44 or 46 and the measuring beam router 32.

The test object 34 is mounted within the environmental modifier 48, which is preferably arranged as a heat regulator including a radiant heat source (not shown) and an array of thermistors (also not shown) for monitoring temperature variations of the test object 34. For example, the environmental modifier 48 can provide for varying the temperature of the test object 34 throughout a range between 0 degrees Celsius and 100 degrees Celsius, although other ranges can be adopted for other applications. The environmental modifier 48 also preferably produces a temperature-variation measuring signal corresponding to the temperature variation induced in the test object 34.

Figure 3:
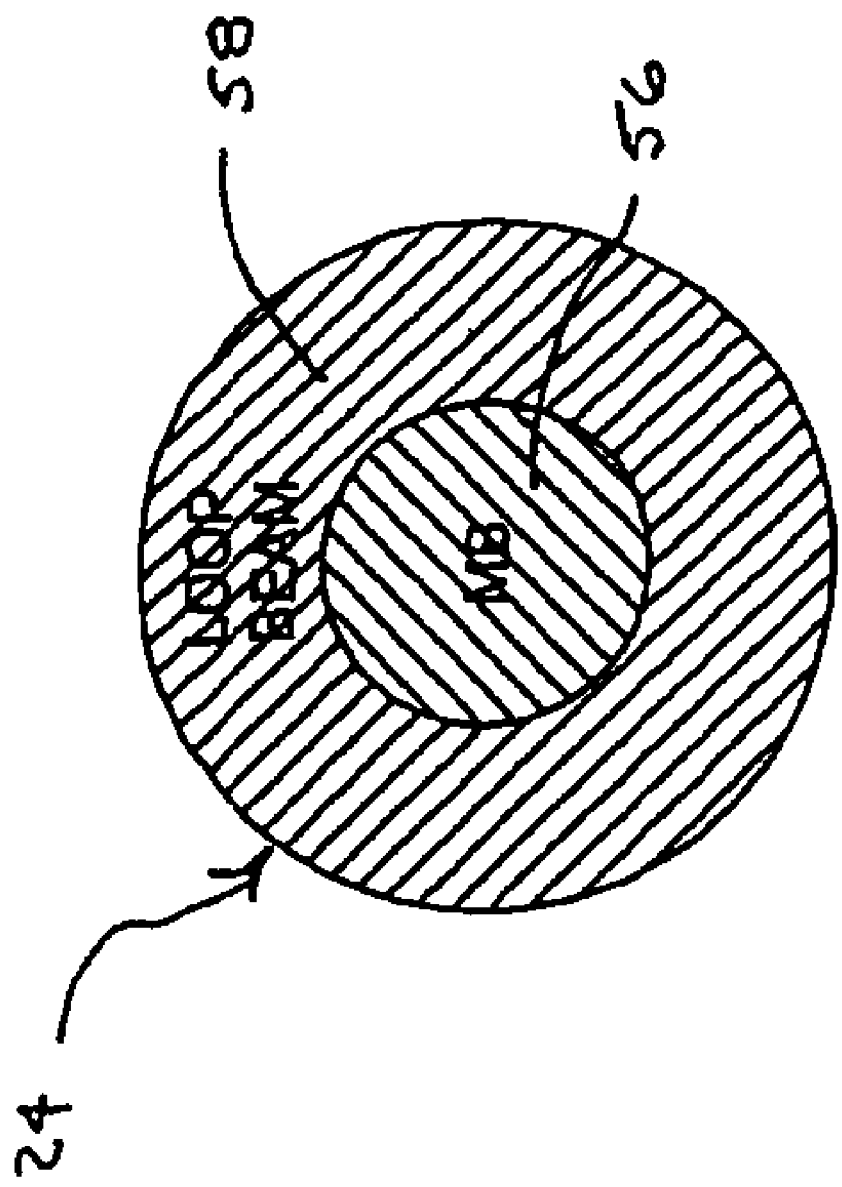
FIG. 3 shows a cross section of the measuring beam with a central core occupied by an object beam and an outer annulus occupied by a loop beam.

The measuring beam 24 returns to the main beam router 16 as the spatially distinguished object and loop beams 56 and 58 sharing the same frequency ($f_2$) and linear polarization (p). As shown in FIG. 3, the returning object and loop beams 56 and 58 occupy different transverse areas of the original measuring beam 24. The object beam 56 occupies the central core of the measuring beam 24 and contains information about dimensional changes of both the test object 34 and the measuring loop 30, and the loop beam 58 occupies a surrounding annulus of the measuring beam 24 and contains information about dimensional changes of the measuring loop 30. The transverse shape of the object beam 56 is largely determined by the shape of the opposite side faces 38 and 40 of the test object 34. The transverse shape of the loop beam 58 is largely determined by what remains of the measuring beam 24.

Figure 4:
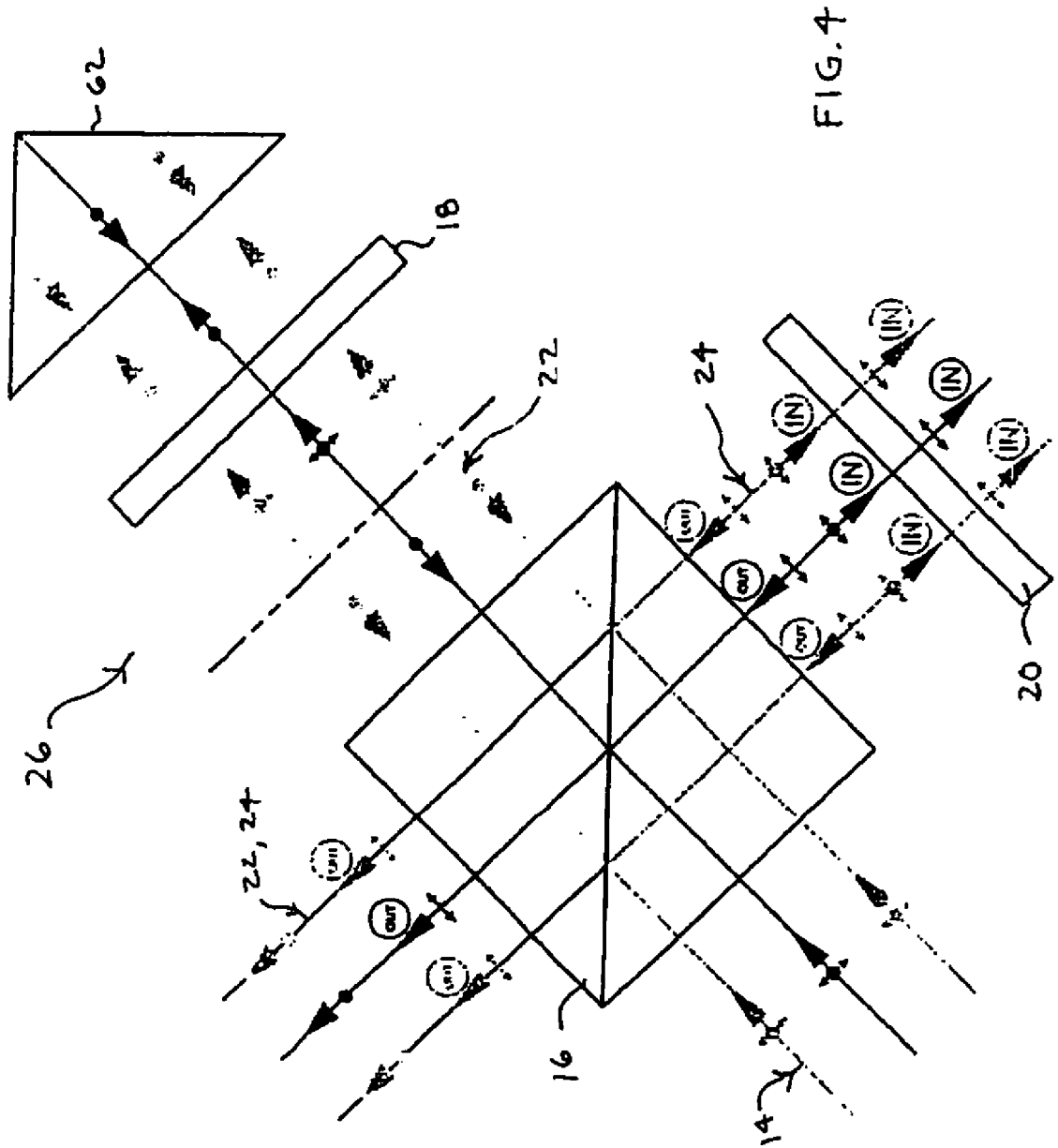
FIG. 4 is a diagram of a reference arm at a main beam router of the instrument.
Figure 5:
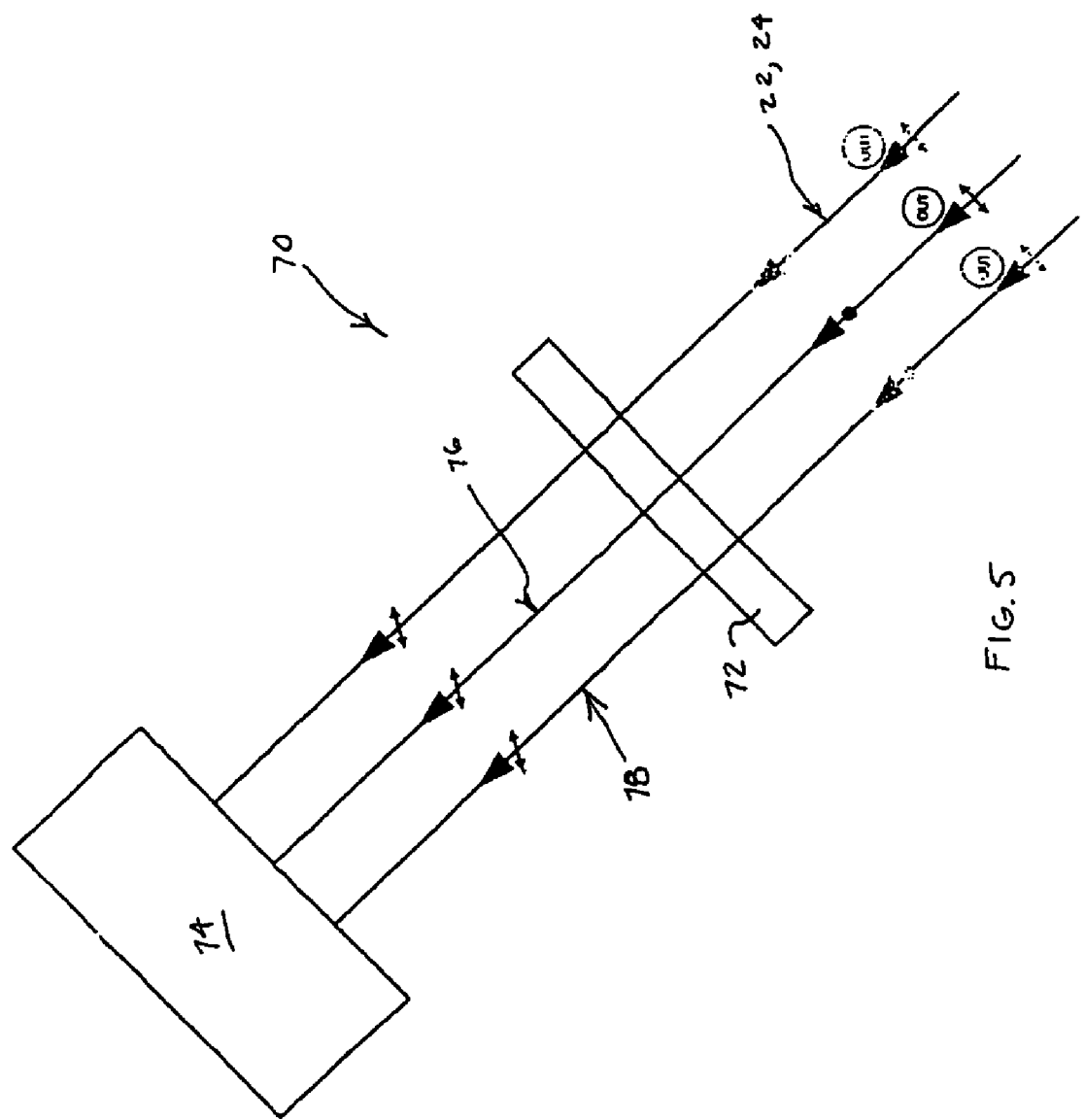
FIG. 5 is a diagram of a data acquisition system also connected to the main beam router.

The reference arm 26, as best seen in FIG. 4, includes in addition to the polarizer 18 a retroreflector 62 for returning the single-frequency ($f_1$) reference beam 22 to the main beam router 16. A portion of the single-frequency ($f_1$) reference beam 22 is reflected by the main beam router 16 into the path of a portion of the returning single-frequency ($f_2$) measuring beam 24 that transmits through the main beam router 16. The overlapping single-frequency ($f_1$) reference beam 22 and single-frequency ($f_2$) measuring beam 24 propagate toward a data acquisition system 70 (see FIG. 5) as orthogonally polarized beams. En route to a detector module 74 of the data acquisition system 70, the orthogonally polarized reference and test beams 22 and 24 encounter a polarizer 72 oriented at approximately 45 degrees to both orthogonal polarizations (s and p) for extracting common polarization components that enable the two beams to interfere with each other producing a heterodyne beat frequency equal to the frequency difference (f1-f2) between the reference and measuring beams 22 and 24.

Two heterodyne signal beams 76 and 78 are formed between the polarization-matched reference and measuring beams 22 and 24. A first 76 of the two heterodyne signal beams is formed between the object beam 56 and a matching core portion of the reference beam 22, and a second 78 of the two heterodyne signal beams is formed between the loop beam 58 and a matching annular portion of the reference beam 22. The detector module 74 physically separates the two heterodyne signal beams 76 and 78.

The detector module 74 as shown in FIGS. 6 and 6A includes an aperture mask 80 that (a) separates transverse areas of the overlapping reference and measuring beams 22 and 24 into a central core portion 82 corresponding to the first heterodyne signal beam 76 and an outer annulus portion 84 corresponding to the second heterodyne signal beam 78 and (b) eliminates any areas of spatial overlap or ambiguity between the two heterodyne signal beams 76 and 78. A transparent wedge 86 with a hollow central aperture 88 produces an angular separation between the central core portion 82 and the outer annulus portion 84. The central core portion 82 transmits through the central aperture 88 without change to a convex lens 90 that focuses the central core portion 82 containing the heterodyne signal 76 incident upon an optical fiber 96 located along a common optical axis 94 of the wedge 86 and the lens 90. The outer annulus portion 84 containing the heterodyne signal 78 refracts through the wedge 86 and is focused by the convex lens 90 upon an optical fiber 98 that is offset from the optical axis 94.

Figure 7:
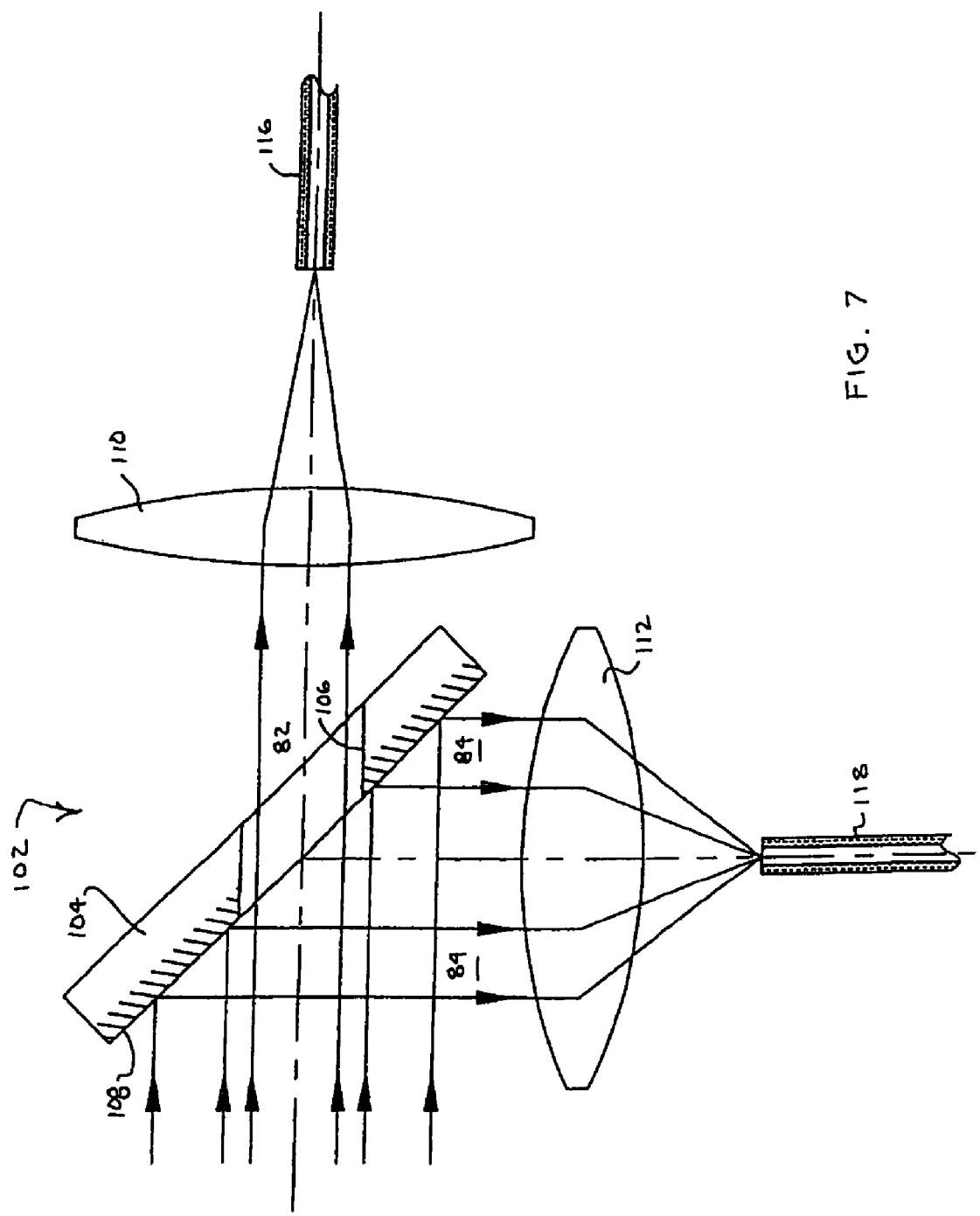
FIG. 7 is a depiction of an alternative detector module for separately detecting different transverse portions of a combined measuring and reference beam.

An alternative detector module 102 is shown in FIG. 7. A modified beamsplitter 104 functions as both an aperture mask and an angular separator for distinguishing the central core portion 82 from the outer annulus portion 84 of the overlapping reference and measuring beams 22 and 24. The beamsplitter 104 includes distinct transmissive and reflective sections 106 and 108. The transmissive section 106 is formed by a through hole, and the reflective section 108 is formed by a remaining reflective surface. The central core portion 82, which embodies the first heterodyne signal beam 76, transmits directly through the transmissive section 106 of the beamsplitter 104 to a convex lens 110 that focuses the central core portion 82 incident upon the optical fiber 116. The outer annulus portion 84, which embodies the second heterodyne signal 78, reflects from the reflective section 108 of the beamsplitter 104 to another convex lens 112 that focuses the outer annulus portion 84 incident upon the optical fiber 118.

The optical fibers 96, 98 or 116, 118 convey the two heterodyne signal beams 76 and 78 to opto-electronic detectors (not shown) that convert the heterodyne signal beams 76 and 78 into corresponding heterodyne electronic signals occupying two separate electronic channels. Alternatively, the detector module 74 could be arranged to focus the separated heterodyne signal beams 76 and 78 directly onto similar opto-electronic detectors. The data acquisition system 70 also includes processing capability for synchronously demodulating the two corresponding heterodyne electronic signals against an electronic reference signal at the common beat frequency. Phase variations of the corresponding heterodyne electronic signals from the electronic reference signal are interpreted as displacement-measuring signals relating to optical path length variations associated with the test object 34 and the measuring loop 30.

A data processor 120 manipulates the displacement-measuring signals with each other for distinguishing displacements of the test object 34 from displacements of the measuring loop 30 and makes associations with the temperature variation-measuring signal to produce a measurement of the displacement of the test object 34 as a function of its temperature variation.

The heterodyne signal beam 76 monitors changes in the optical path length of the object beam 56. The approximate optical path length $OPL_{OB}$ of the object beam 56 through the measuring loop 30 is given by the following equation, which is simplified for initial presentation by not accounting for phase changes upon reflection:

$$OPL_{OB} = 4(L_L + L_R) + 2L_{RETRO}$$

where with reference to FIG. 8, $L_L$ refers to an optical path length designated O-A-B between the measuring beam router 32 and the face 38 of the test object 34, $L_R$ refers to an optical path length designated O-A'-B' between the measuring beam router 32 and the face 40 of the test object 34, and $L_{RETRO}$ refers to a distance between the measuring beam router 32 and the retroreflector 60. The object beam 56 traverses each the lengths LL and LR four times (i.e., two round trips from the measuring beam router 32 to each of the opposite side surfaces 38 and 40 of the test object 34) and traverses the length $L_{RETRO}$ twice (i.e., one round trip between the measuring beam router 32 and the retroreflector 60).

A change in the optical path length $\Delta OPL_{OB}$ of the object beam 56 through the measuring loop 30 discernable from the first heterodyne signal beam 76 is a combination of the changes $\Delta L_L$, $\Delta L_R$, $\Delta L_{RETRO}$ in the referenced optical path lengths traversed by the object beam 56 through the measuring loop 30 as reflected in the following expression:

$$\Delta OPL_{OB} = 4(\Delta L_L + \Delta L_R) + 2\Delta L_{RETRO}$$

As further referenced by FIG. 8, the changes in the path lengths $\Delta L_L$, $\Delta L_R$ to and from the test object 34 can be due to either changes in the measuring loop structure $\Delta L_{S1}$, $\Delta L_{S2}$, which sum to $\Delta L_{STRUCTURE}$ or to changes in the dimensions of the test object 34 as referenced by the individual position changes $\Delta L_1$, $\Delta L_1$ of the opposite end faces 38 and 40 of the test object 34, which sum to $\Delta L_{OBJECT}$. The two equalities reproduced below express this relationship.

$$\Delta L_L = \Delta L_{S1} + \Delta L_1$$

$$\Delta L_R = \Delta L_{S2} + \Delta L_2$$

By substitution, the optical path length changes $\Delta OPL_{OB}$ of the object beam 56 can be rewritten as follows:

$$\Delta OPL_{OB} = 4(\Delta L_{S1} + \Delta L_{S2} + \Delta L_1 + \Delta L_2) + 2\Delta L_{RETRO}$$

or $$\Delta OPL_{OB} = 4(\Delta L_{STRUCTURE} + \Delta L_{OBJECT}) + 2\Delta L_{RETRO}$$

In the absence of spurious optical path length changes in the measuring loop, i.e., $\Delta L_{STRUCUTURE} = \Delta L_{RETRO} = 0$, the terms representing error sources would vanish and the measured change in the optical path length by the object beam 56 could be attributable solely to the dimensional changes $\Delta L_{OBJECT}$ of the test object 34. The spurious optical path length changes in the measuring loop 30 are generally not zero, but are measured by the loop beam 58.

The optical path length $OPL_{LP}$ of the loop beam 58 is given by the following expression:

$$OPL_{LP} = 4(L_L + L_R + L_{NOMINAL}) + 2L_{RETRO}$$

where $L_{NOMINAL}$ is the nominal length of the test object 34 from which any changes in the dimensions of the test object 34 are referenced.

The change in optical path length $\Delta OPL_{LP}$ discernable from the second heterodyne signal beam 78 is given by the next expression:

$$\Delta OPL_{LP} = 4(\Delta L_L + \Delta L_R + \Delta L_{NOMINAL}) + 2\Delta L_{RETRO}$$

In contrast to the optical path length changes undergone by the object beam 56, the lengths $\Delta L_L$, $\Delta L_R$ within the measuring loop 30 traversed by the loop beam 58 are only affected by changes in the measuring loop itself $\Delta L_{S1}$, $\Delta L_{S2}$ and not by any changes in the test object 34. The loop beam 58 bypasses the test object 34 and is not influenced by any dimensional changes of the test object 34. Appropriate substitutions allow the change in the optical path length $\Delta OPL_{LP}$ of the loop beam 58 to be rewritten as the following two expressions:

$$\Delta OPL_{LP} = 4(\Delta L_{S1} + \Delta L_{S2} + \Delta L_{NOMINAL}) + 2\Delta L_{RETRO}$$

$$\Delta OPL_{LP} = 4(\Delta L_{STRUCTURE} + \Delta L_{NOMINAL}) + 2\Delta L_{RETRO}$$

The optical path length changes $\Delta OPL_{LP}$ undergone by the loop beam 58 independently of the test object 34 are largely a measure of the spurious displacement terms $\Delta L_{STRUCUTURE}$, $\Delta L_{RETRO}$ found in the earlier expression for the optical path length variation $\Delta OPL_{OB}$ of the object beam 56. Thus, the dimensional changes $\Delta L_{OBJECT}$ of the test object 34 can be calculated by subtracting the measure of the optical path length changes $\Delta OPL_{LP}$ derived from the loop beam 58 from the measure of the optical path length changes $\Delta OPL_{OB}$ derived from the object beam 56 as follows:

$$\Delta L_{OBJECT} = \frac{(\Delta OPL_{OB} - \Delta OPL_{LP})}{4} + \Delta L_{NOMINAL}$$

The final term $\Delta L_{NOMINAL}$ is a residual source of some uncertainty that arises because the path traveled by the loop beam 58 parallels the path traveled by the measuring beam 56 except in the portion occupied by the test object 34. The path traveled by the loop beam 58 bypassing the test object 34 is through free space. The only non-common mode influence on this dimension $L_{NOMINAL}$ is a change in refractive index. However, by operating the interferometer in a vacuum, the residual spurious influence of this term is expected to be small.

As alluded to earlier, a more refined model of the optical path length changes $\Delta OPL_{OB}$, $\Delta OPL_{LP}$ undergone by the measuring and loop beams 56 and 58 requires consideration of the phase changes brought about by encounters with optical components, including the test object 34, along the measuring loop 30. A table listing the changes in phase change terms follows.

Table of Changes in Phase Changes in Measuring Loop

| Symbol | Description |
|---|---|
| $\Delta \phi_R$ | Change in phase change on reflection at measuring beam router |
| $\Delta \phi_{T1}$ | Change in phase change on transmission through measuring beam router in first direction |
| $\Delta \phi_{T2}$ | Change in phase change on transmission through measuring beam router in second direction |
| $\Delta \phi_V$ | Change in phase change on reflection at beam director |
| $\Delta \phi_{RETRO}$ | Change in phase change on reflection at retroreflector |
| $\Delta \phi_{OBJECT}$ | Change in phase change on reflection at opposite side surfaces of the test object |

The various change in phase change terms for transmission and reflection at the measuring beam router 32 are referenced in FIGS. 9A and 9B. All of the change in phase change terms are expressed in units of length and can be directly incorporated into the expressions for the optical path length changes $\Delta OPL_{OB}$, $\Delta OPL_{LP}$ undergone by the measuring and loop beams 56 and 58 as follows:

$$\Delta OPL_{OB} = 4(\Delta L_{STRUCTURE} + \Delta L_{OBJECT} + \Delta \phi_{OBJECT}) + 2(\Delta_{RETRO} + \Delta \phi_{T1} + \Delta \phi_{T2} + \Delta \phi_R) + 8\Delta \phi_V + \Delta \phi_{RETRO}$$

$$\Delta OPL_{LP} = 4(\Delta L_{STRUCTURE} + \Delta L_{NOMINAL}) + 2(\Delta L_{RETRO} + \Delta \phi_{T1} + \Delta \phi_{T2} + \Delta \phi_R) + 8\phi_V + \Delta \phi_{RETRO}$$

The dimensional change $\Delta L_{OBJECT}$ of the test object 34 can still be calculated by subtracting the optical path length changes $\Delta OPL_{LP}$ undergone by the loop beams 58 from the optical path length changes $\Delta OPL_{OB}$ undergone by the measuring beam 56, leaving only one additional residual term as follows:

$$\Delta L_{OBJECT} = \frac{(\Delta OPL_{OB} - \Delta OPL_{LP})}{4} + \Delta L_{NOMINAL} - \Delta \phi_{OBJECT}$$

All of the change in phase change terms with the exception of the change in phase change $\Delta \phi_{OBJECT}$ undergone by reflections from the test object 34 are canceled from the above expression because the measuring and loop beams 56 and 58 encounter all the same other optical components of the measuring loop 30 by the same number of times.

Any changes in phase change $\Delta \phi_{OBJECT}$ at the opposite side faces 38 and 40 of the test object associated with the induced changes in the test object 34, such as changes in temperature, can be managed as systematic errors that can be estimated by taking additional measurements. One such estimation technique is based on the method described in a paper by M. Okaji, N. Yamada, K. Nara, and H. Kato entitled "Laser interferometric dilatometer at low temperatures: application to fused silica SRM 739," *Cryogenics* 35, pp. 887-891, 1995, which is hereby incorporated by reference. This method requires an instrument, such as the instrument 1 0, that accommodates the measurement of test objects of different lengths. The method is described below.

Systematic errors $\Delta L_{SYSTEMATIC}$ can be related to the measured vs. actual changes in dimension $\Delta L_{MEASURED}$, $\Delta L_{ACTUAL}$ as follows:

$$\Delta L_{MEASURED} = \Delta L_{ACTUAL} + \Delta L_{SYSTEMATIC}$$

The systematic error $\Delta L_{SYSTEMATIC}$ can be cancelled by measuring specimens of different lengths, provided that the systematic error is repeatable from one measurement to another. Two independent measurements $\Delta L_{MEASURED}, 1$, $\Delta L_{MEASURED}, 2$ subject to the same systematic error $\Delta L_{SYSTEMATIC}$ can be referenced as follows:

$$\Delta L_{MEASURED}, 1 = \Delta L_{ACTUAL}, 1 + \Delta L_{SYSTEMATIC}$$

$$\Delta L_{MEASURED}, 2 = \Delta L_{ACTUAL}, 2 + \Delta L_{SYSTEMATIC}$$

Assuming that the systematic error $\Delta L_{SYSTEMATIC}$ is the same for both measurements, the difference between the measured values is equal to the difference between the actual values as expressed below:

$$\Delta L_{MEASURED}, 1 - \Delta L_{MEASURED}, 2 = \Delta L_{ACTUAL}, 1 - \Delta L_{ACTUAL}, 2$$

The right side of the above equality represents the net length change of a virtual specimen whose length is equal to the difference in length between the two actual specimens. This method of error estimation is possible in an instrument that permits the measurement of test objects of different lengths with minimal changes to the rest of the instrument. This method also relies on the assumption that the absolute change in dimension of the test object scales with the test object length.

The heterodyne measurements include a residual term relating to change in phase change $\Delta \phi_{OBJECT}$ upon reflection from the opposite side surfaces 38 and 40 of the test object 34. As a systematic error, the residual term for change in phase change $\Delta \phi_{OBJECT}$ at the object 34 can be removed by making a plurality of measurements. The additional measurements can be made either separately as described above or simultaneously by modifying the loop beam or at least a portion of the loop beam to include similar reflective surfaces.

For example, instrument 210, which is depicted by FIG. 10, is based on the instrument 10 of FIG. 1 but features a modified measuring loop 212 including a thin dual-sided reflector 214 in the path of a loop beam 228. Preferably, the dual-sided reflector 214 is made of the same ultra-low thermal expansion material as the test object 34 with opposite side surfaces 218 and 220 that are polished, coated, or otherwise prepared for reflection similar to the opposite side surfaces 38 and 40 of the test object 34. The object and loop beams 226 and 228 remain optically balanced. In fact, the object and loop beams 226 and 228 encounter the same other components of the measuring loop 212 in the same order.

If sufficiently thin, any dimensional changes of the reflector 214 can be ignored. Assuming also that phase changes at the reflective surfaces 218 and 220 of the reflector 214 match the phase changes at the reflective surfaces 38 and 40 of the test object 34, the dimensional changes in the test object 34 can be calculated as follows:

$$\Delta L_{OBJECT} = \frac{(\Delta OPL_{OB} - \Delta OPL_{LP})}{4} + \Delta L_{NOMINAL}$$

Here, only the residual term remaining is the term $\Delta L_{NOMINAL}$ for propagating through the free space parallel to the test object 34, and this term is not expected to contribute significant error.

Prior to engaging in any measurements of the test object, the two frequencies $f_1$ and $f_2$ emitted by the laser source 12 can be monitored to detect and compensate or correct for any variations. For example, either one of the two frequencies could be combined with a frequency-stabilized laser source, such as an iodine-stabilized HeNe laser, and monitored for changes in the resulting a heterodyne signal.

Although described with respect to particular embodiments, those of skill in the art will appreciate that the invention can be practiced in a wide number of instrument configurations, particularly where object and loop beams traverse a common measuring loop for detecting dimensional changes in a test object and the same object beam reflects from both opposite side surfaces of a test object.

What is claimed is:

1. An optical instrument for measuring dimensional changes of a test object between two opposite side faces of the test object comprising
    a measuring loop having a plurality of optical components and a mounting for the test object,
    a beam routing system for routing a measuring beam from a beam source to the measuring loop and from the measuring loop to a data acquisition system;
    the optical components of the measuring loop being arranged (a) for circulating a first transverse portion of the measuring beam as an object beam that encounters both of the opposite side faces of the test object and the optical components between entering and exiting the measuring loop and (b) for circulating another transverse portion of the measuring beam as a loop beam that encounters the optical components without encountering the two opposite side faces of the test object between entering and exiting the measuring loop, and
    the data acquisition system providing for directly or indirectly comparing the object and loop beams to distinguish length variations between the two opposite side faces of the test object and path length variations of the measuring loop.

2. The instrument of claim 1 in which the object and loop beams encounter each of the optical components of the measuring loop the same number of times.

3. The instrument of claim 2 in which the object beam encounters each of the two opposite side faces of the test object more than one time.

4. The instrument of claim 1 in which the opposite side faces of the test object are substantially flat and at least partially reflective.

5. The instrument of claim 4 in which the opposite side faces of the test object extend substantially parallel to one another and overlap each other along the measured length of the test object.

6. The instrument of claim 1 further comprising an environmental modifier for subjecting the test object to varying conditions within the measuring loop.

7. The instrument of claim 6 in which the environmental modifier includes a heat regulator for varying the temperature of the test object.

8. The instrument of claim 6 in which the data acquisition system collects data regarding the length variations of the test object at the different conditions of the test object imposed by the environmental modifier.

9. The instrument of claim 1 in which the object and loop beams have the same beam frequencies and the beam routing system combines the object and loop beams with a different frequency reference beam to form heterodyne signals that vary with path length variations between the object and loop beams.

10. The instrument of claim 9 in which the measuring loop includes a polarizing beamsplitter for directing the measuring beam into the measuring loop as linearly polarized object and loop beams and waveplates located between the beamsplitter and each of the two opposite side faces of the test object for orthogonally rotating the polarization of the object and loop beams between encounters with the polarizing beamsplitter.

11. The instrument of claim 10 further comprising a retroreflector optically connected to the beamsplitter for returning the object and loop beams to the measuring loop so that the object beam encounters each of the two opposite side faces of the test object more than one time and so that the loop beam encounters each of the optical components of the measuring loop the same number of times as the object beam.

12. The instrument of claim 1 further comprising a reflector located within the measuring loop for reflecting the loop beam without further reflecting the object beam.

13. The instrument of claim 12 in which the reflector has a de minimus thickness in the direction of beam propagation.

14. An optical instrument for measuring dimensional changes of a test object between two opposite side faces of the test object comprising
    a light source for introducing first and second beams of different primary frequencies,
    a beam routing system for routing the first and second frequency beams including routing the first frequency beam into a measuring arm,
    a measuring loop within the measuring arm having a plurality of optical components and a mounting for the test object,
    the optical components being arranged for circulating a first transverse portion of the first frequency beam through encounters with both the plurality of optical components and the two opposite side faces of the test object and for circulating a second transverse portion of the first frequency beam through encounters with the same optical components without encountering the two opposite side faces of the test object, and the beam routing system also providing for combining the first and second transverse portions of the first frequency beam with the second frequency beam for producing heterodyne signals that can be evaluated for distinguishing length variations between the two opposite side faces of the test object from path length variations of the remaining measuring loop.

15. The instrument of claim 14 further comprising an environmental modifier for subjecting the test object to varying conditions within the measuring loop.

16. The instrument of claim 15 in which the environmental modifier includes a heat regulator for varying the temperature of the test object.

17. The instrument of claim 15 further comprising a data acquisition system that evaluates the length variations between the two opposite side faces of the test object at the different conditions of the test object imposed by the environmental modifier.

18. The instrument of claim 14 in which the first and second transverse portions of the first frequency beam encounter each of the optical components of the measuring loop the same number of times.

19. The instrument of claim 14 in which the beam routing system routes the second frequency beam into a reference arm.

20. The instrument of claim 19 further comprising a beam discriminator for preventing the second frequency beam from entering the measuring loop.

21. The instrument of claim 20 in which the beam discriminator is a first of a plurality of beam discriminators and a second of the beam discriminators prevents the first frequency beam from propagating through the reference arm.

22. The instrument of claim 21 in which the first and second frequency beams are orthogonally polarized and the first and second beam discriminators are polarizers.

23. The instrument of claim 14 in which the measuring loop includes a beamsplitter for directing the first frequency beam into and out of the measuring loop.

24. The instrument of claim 23 in which the measuring loop contains waveplates for orthogonally rotating the polarization of the first measuring beam between encounters with the beam splitter.

25. The instrument of claim 23 in which the measuring loop contains directional mirrors that direct the first transverse portion of the first frequency beam into alignment with the two opposite side faces of the test object and that direct the second transverse portion of the first frequency beam along a route that includes the beamsplitter and the directional mirrors.

26. The instrument of claim 23 further comprising a retroreflector optically connected to the beamsplitter for returning the first frequency beam to the measuring loop so that the first transverse portion of the first frequency beam encounters each of the two opposite side faces of the test object more than one time.

27. The instrument of claim 26 in which the first and second transverse portions of the first measuring beam encounter each of the optical components of the measuring loop the same number of times.

28. The instrument of claim 14 further comprising a reflector that interrupts the loop beam.

29. The instrument of claim 28 in which the reflector has a de minimus thickness in the direction of beam propagation.

* * * * *